United States Patent [19]
McMinn

[11] Patent Number: 5,879,392
[45] Date of Patent: Mar. 9, 1999

[54] KNEE PROSTHESIS

[76] Inventor: Derek James Wallace McMinn, Calcot Farm, Calcot Hill, Clent, Stourbridge, DY9 9RX, England

[21] Appl. No.: 840,372

[22] Filed: Apr. 29, 1997

[30] Foreign Application Priority Data

May 8, 1996 [GB] United Kingdom ............. 9609609

[51] Int. Cl.$^6$ ........................................... A61F 2/38
[52] U.S. Cl. ................................................ 623/20
[58] Field of Search ................................... 623/20

[56] References Cited

U.S. PATENT DOCUMENTS

| | | | |
|---|---|---|---|
| 4,213,209 | 7/1980 | Insall | 623/20 |
| 4,224,697 | 9/1980 | Murray | 623/20 |
| 4,298,992 | 11/1981 | Burstein et al. | |
| 5,330,534 | 7/1994 | Herrington | 623/20 |
| 5,549,686 | 8/1996 | Johnson | 623/20 |
| 5,571,197 | 11/1996 | Insall | 623/20 |
| 5,658,344 | 8/1997 | Hurlburt | 623/20 |

FOREIGN PATENT DOCUMENTS

| | | |
|---|---|---|
| 0 349 173 | 1/1990 | European Pat. Off. |
| 1 534 263 | 11/1978 | United Kingdom. |
| 2 296 443 | 7/1996 | United Kingdom. |
| WO 96/03097 | 2/1996 | WIPO. |

OTHER PUBLICATIONS

Mr. A.J. Polyzoides, FRCS and Dr. A. Tsakonas, MD; *The Rotaglide$^{RTM}$ Total Knee System*, Corin Medical Ltd 1997.

Primary Examiner—Michael J. Milano
Attorney, Agent, or Firm—Fishman, Dionne, Cantor & Colburn

[57] ABSTRACT

A knee prosthesis comprising a femoral component, a tibial component and a meniscal component therebetween, a stabilising peg extending from the tibial component through an elongated slot in the meniscal component and into an opening in the femoral component between a pair of condylar members thereof. The part of the peg extending through the slot allows the meniscal component to rotate and also to move linearly about the peg along one path, whilst the part of the peg in said opening engages cam surfaces on a projection between said condylar members as the knee is flexed, in use, and said linear movement of the meniscal component occurs.

18 Claims, 3 Drawing Sheets

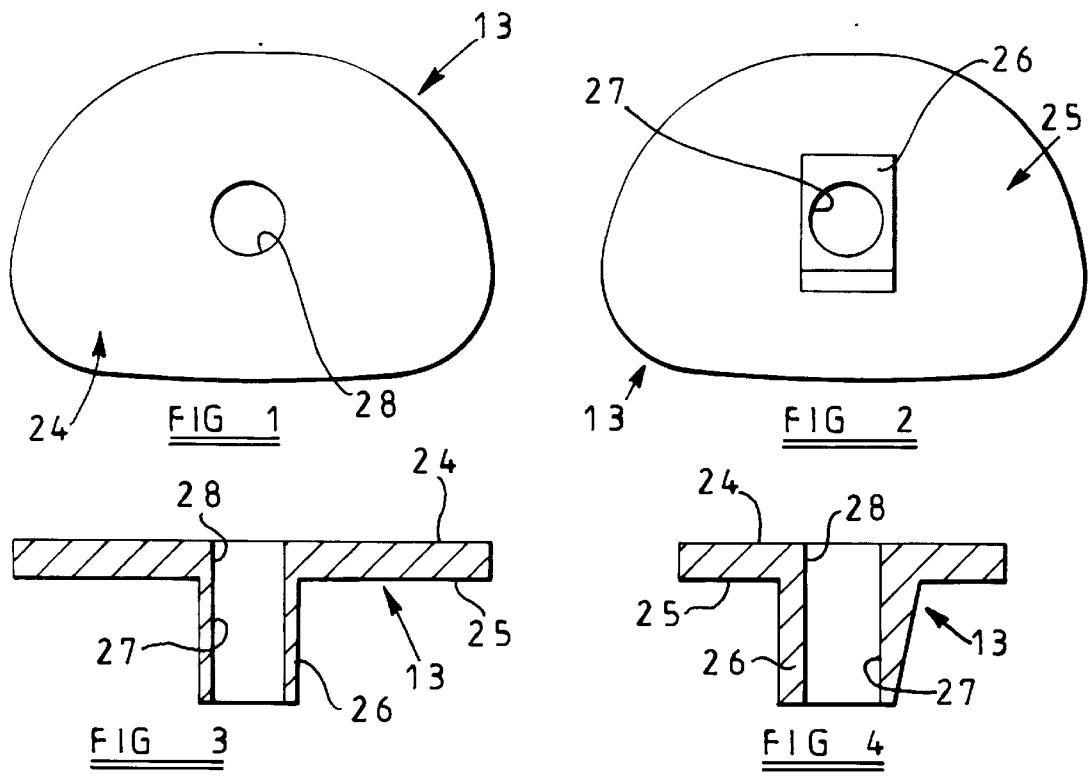
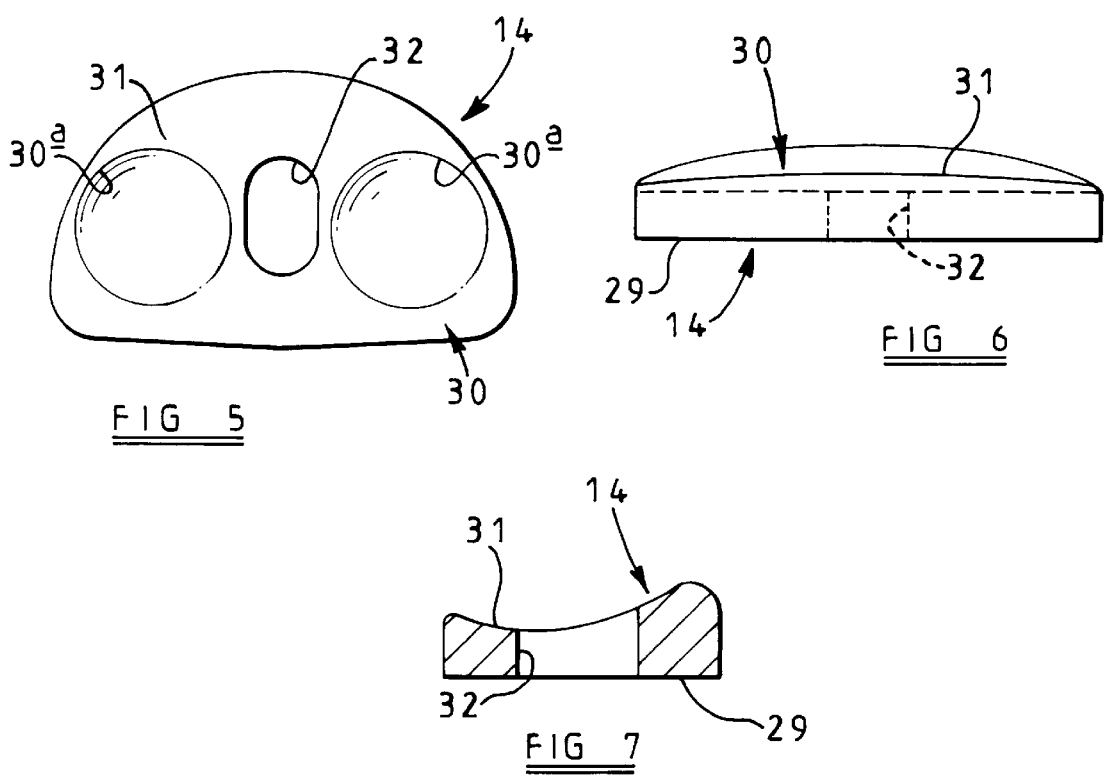

KNEE PROSTHESIS

BACKGROUND OF THE INVENTION

1. Field of the Invention

This invention relates to a knee prosthesis for fitting to a patient as a replacement knee joint.

2. Prior Art

Modern total knee replacement involves the resurfacing of the femoral condyles with a metallic component, roughly approximating to the shape of the anatomical femoral condyles, and resurfacing the tibial plateau with a polyethylene component having a metallic base plate. Conformity between the polyethylene of the tibial component and the metallic femoral component has historically been a troublesome area. Ideally the femoral component should be congruent with the top of the tibial component in order to minimise polyethylene wear. The difficulty, however, is that the knee joint does not act as a fixed axis hinge. During normal movements of the knee, rotation of the femur upon the tibia occurs, and roll back of the femoral condyles upon the tibia occurs, particularly when the knee is flexed.

UK Patent No 1,534,263 discloses a knee joint device formed by a femoral component, a floating plastics material meniscal component, and a flat topped tibial component. This device allowed congruency between the femoral and meniscal components, but since the meniscal component was free to move antero-posteriorly and to rotate, rotational and sheer stresses were not generated at the tibial implant fixation interface and loosening did not occur. Moreover wear of the polyethylene was found to be low. However this device suffered from the disadvantage that under certain circumstances posterior or medio lateral dislocation could occur, with the meniscal component possibly being displaced into the synovium.

Whilst the device of UK Patent No 1,534,263 was generally concerned with a replacement joint to address unicompartmental disease (medial arthritis of the knee), where the cruciate ligaments and lateral compartment of the knee were left untouched, it is common practice to perform a total knee replacement, where the lateral component of the knee is also resurfaced and the anterior cruciate ligament or both cruciate ligaments are resected. A commonly employed total knee replacement is the Insall Burstein replacement in which both cruciate ligaments are resected and a posterior stabilised design of knee replacement is inserted. The provision of a bearing in the form of a cam mechanism between the femoral component and the polyethylene tibial component means that with increased flexion of the knee increased posterior translation of the femoral component upon the tibia occurs, partially simulating the normal kinematics of the knee. The cam mechanism replaces the function of the cruciate ligaments. However although the kinematics in terms of femoral roll back are adequately addressed, the bearing between the tibial and femoral components is incongruent, and therefore theoretically undesirable, resulting in high contact stress, leading to plastics wear.

Another type of total knee replacement involves retention of the posterior cruciate ligament, with a polyethylene meniscus, broadly congruent with the femoral component, being allowed to rotate and/or slide on a polished metal tibial plateau, thereby addressing both the issue of high contact stress and also tibial loosening. A disadvantage of this type of knee replacement relates to the function of the posterior cruciate ligament, with the anterior cruciate ligament resected. For the cruciate ligaments to act effectively, both the anterior and the posterior ligaments do have to be present in the knee, as they represent a four bar linkage between the femur and the tibia. It has been shown that isolated retention of the posterior cruciate ligament does not adequately allow the normal kinematics of the knee to occur. Accordingly upon flexion of the knee, instead of the normal posterior translation of the femur upon the tibia, the reverse is often found to occur, whereby the femoral component abnormally translates forwards on the tibia, with, in the worst case, posterior dislocation.

This has two undesirable side effects. Firstly the patellofemoral contact pressures are abnormally increased, thus increasing the potential for pain at the front of the knee, or loosening of the patellar component, or fracture of the patella. Secondly a patient with this abnormal anterior translation may not be capable of full flexion of the knee after replacement, as soft tissue impingement between the femur and the tibia posteriorly can occur when the normal femoral roll back in flexion does not happen.

SUMMARY OF THE INVENTION

An object of the invention is to provide an improved knee prosthesis in which at least some of the above mentioned disadvantages are reduced or overcome.

According to the present invention there is provided a knee prosthesis comprising a femoral component for securement to the femur, a tibial component for securement to the tibia, a bearing component between the femoral and tibial components, the femoral component and the bearing component having respective curved articulatory bearing surfaces of congruent form, and there being location means extending from the tibial component, through the bearing component and into an opening defined by the femoral component, the bearing component being capable of rotational movement, and also linear movement along one path, about the location means, said linear movement occurring, in use, upon flexion of the knee.

Preferably the location means comprises a peg, the part thereof extending through the bearing component being of circular external cross-section. Desirably said peg part extends through an elongated slot in the bearing component, the width of the slot being such as to prevent relative lateral movement between the peg and the bearing component, in use. Conveniently the external surface of said part of the peg is of metal, preferably polished metal, and the bearing component is of plastics material. Advantageously the peg is separate from, but securely engaged with the tibial component. The peg desirably has a protective tip of plastics material, for example polyethylene, which engages with a surface defined by the femoral component to provide, in use, upon flexion of the knee, a 'cam' action and to limit relative forward motion of the femur and prevent posterior dislocation.

The knee prosthesis thus provides the advantages of a posterior stabilised knee with the 'cam' mechanism thus ensuring normal posterior translation of the femur upon the tibia during flexion of the knee, whilst at the same time allowing congruence between the femoral component and the polyethylene meniscus (bearing component), thus minimising polyethylene wear and minimising tibial rotational and shear stresses.

BRIEF DESCRIPTION OF THE DRAWINGS

The invention will now be described, by way of example, with reference to the accompanying drawings, in which:

FIG. 1 is a top plan view of a tibial component of a knee prothesis of the invention;

FIGS. 2 to 4 are an underside plan view, a longitudinal central sectional view and a lateral central sectional view respectively of the tibial component of FIG. 1;

FIGS. 5 to 7 are a top plan view, a rear view and a lateral central sectional view respectively of a bearing component of the knee prosthesis of the invention;

DETAILED DESCRIPTION OF THE PREFERRED EMBODIMENT

Figure 11:
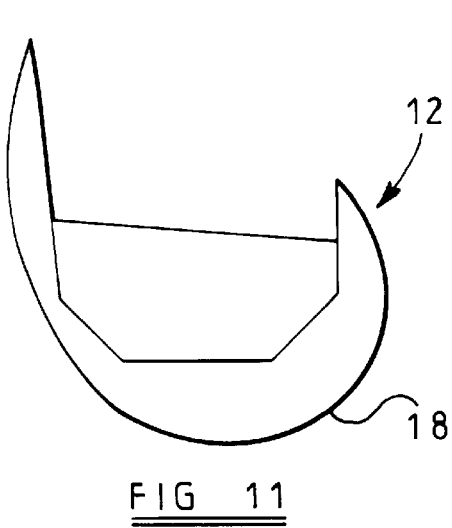
Figure 12:
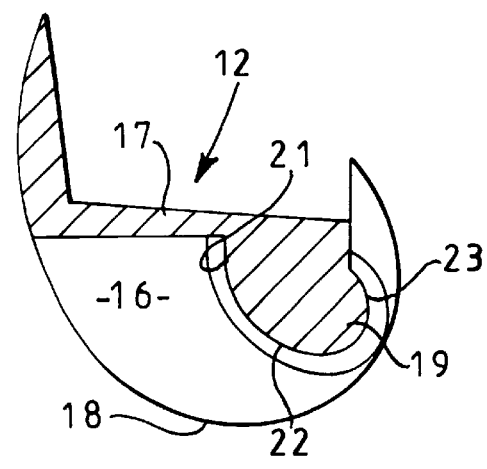
Figure 13:
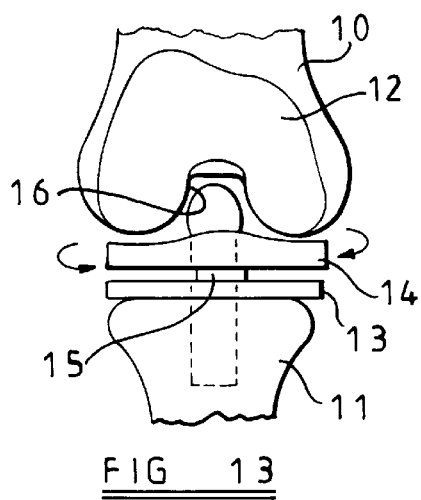
FIG. 13 is a very schematic front view of a knee joint incorporating the knee prosthesis.

In the drawings, FIGS. 1 to 12 relate to the individual component parts of the knee prosthesis of the invention, whilst FIG. 13 very schematically shows the replacement knee joint fitted, in use, at the junction of a femur 10 and a tibia 11 of the knee. For convenience, only the distal end portion of the femur and the proximal end portion of the tibia is shown in each case.

The knee joint device shown in FIG. 13 has some similarity with replacement devices known from the prior art in that it comprises a femoral component 12, a tibial component 13 and a meniscal component 14 disposed between the components 12 and 13. Additionally, however, the replacement knee device also incorporates location means in the form of a stabilising peg 15 which extends through both the tibial component 13 and the meniscal component 14, with an upper end portion thereof being received in an opening 16 in the form of a cavity/notch defined in the femoral component 12. As will be described, the arrangement of the invention allows the meniscal component unconstrained rotation and limited antero-posterior translation.

As will be appreciated from FIG. 13, the knee replacement device shown is of bicondylar form, with the femoral component 12 being a bicompartmental component. This is generally of known form defining a pair of spaced 'rounded' surfaces corresponding substantially to the condyles of the normal femur, the component 12 being a single one-piece construction with the associated pair of condylar parts connected by a bridging portion.

Figure 10:
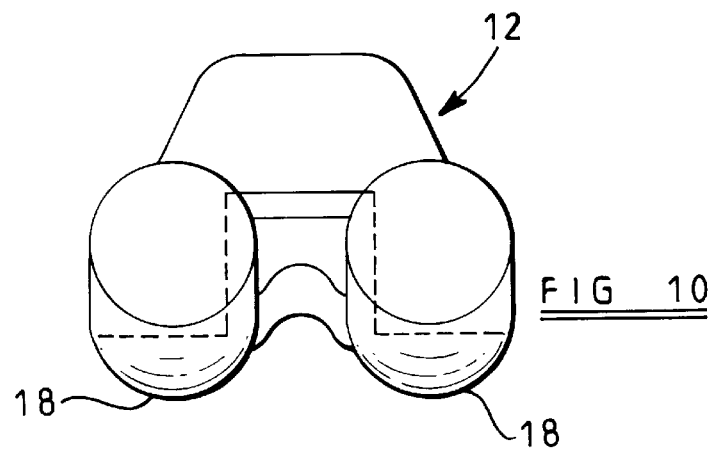

FIGS. 10 to 12 show such a femoral component in more detail, and in particular these views show the bridging portion 17 and the rounded surfaces 18 referred to above. Particularly the surfaces would be hemispherical or at least part-spherical. It will be seen that the bridging portion 17 is formed with an integral, central projection 19 extending in a direction generally parallel to the respective opposite sides of the opening 16, with a free end 20 of the projection terminating short of the surfaces 18 of the femoral component 12 at respective opposite exterior sides of the opening. As can be seen from FIGS. 12 and 14 to 16, the projection is formed at the rear of the bridging portion 17. Centrally of the sides of opening 16, the projection has a flat front surface 21 extending from the bridging portion, this leading to an arcuate surface 22 which extends to the free end 20 where it joins a further arcuate surface 23 which extends to the rear of the projection, the radius of curvature of the surface 23 being greater than that of both the surface 22 and also each of the rounded surfaces 18. As will be described, the surfaces of the projection act as cam surfaces in engagement with the peg 15 upon flexing of the knee in which the replacement knee joint device is fitted.

The femoral component 12 would normally be of metallic material with its lower surface highly polished. Typically it could be of cobalt chrome and would be affixed to the femur by any form of suitable cement adhesion or biological fixation. Although, as described, the femoral component 12, and indeed the device as a whole is described and illustrated as bicondylar, the invention is also applicable to a knee prosthesis where the femoral component is of tricompartmental form in which the bridging portion defines a patellar articular surface. As will be appreciated, the precise form of the femoral component is not critical in terms of the inventive concept, provided it defines an opening into which location means extending from the tibial component and through the bearing component can be received.

The tibial component 13 comprises a bearing body in the form of a generally D-shaped platform of generally uniform thickness. The one-piece component 13 would normally be of a metallic material, such as cobalt chrome. The platform defines an upper planar surface 24 which, as will be described, serves as an articulatory bearing surface. This surface 24 is uppermost, in use, as shown in FIGS. 13 to 16. This upper surface 24 would normally be highly polished. The platform also defines a lower planar surface 25 which is adapted to be secured to the tibia 11, in use, in accordance with similar techniques for those for the femoral component 12, so that the surface 24 serves as a tibial condylar surface replacement. The surface 25 is thus formed with at least one proximal keel 26. It can be seen that this keel is of generally rectangular exterior cross-section, with its front facing shorter side tapered, and with a circular-section bore 27 extending therethrough. A circular section hole 28 extends through the platform of the tibial component 13 from the surface 24 to the surface 25, where it is in direct alignment with the top of the bore 27 and of the same diameter thereas at said junction. In use, the tibial component 13 would be secured to the top of the tibia by cement or other adhesive on the lower surface 25, or alternatively by means of some biological fixation, so that the component 13 is securely fixed to the tibia 11, in use, with the keel 26 extending into a complimentarily shaped opening in the top of the tibia. The fixing would be such as to allow modularity of distal stem design for revision surgery.

Figure 14:
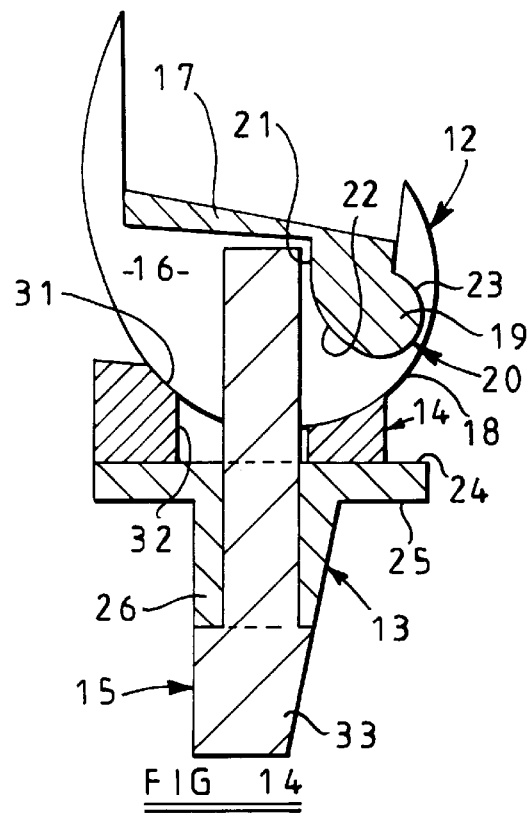
FIGS. 14 to 16 are respective diagrammatic/schematic sectional side views generally showing operation, in use, of the knee prosthesis for aligned, partly flexed and fully flexed relative positions of the tibia and femur.
Figure 15:
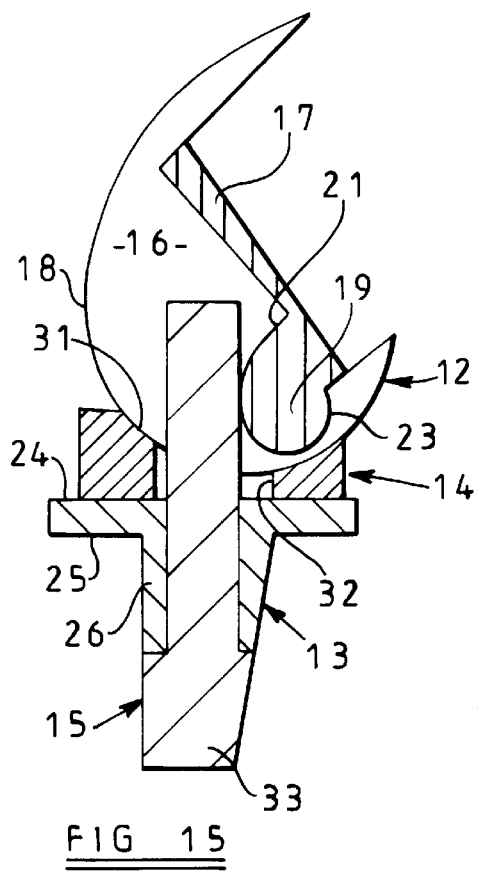
Figure 16:
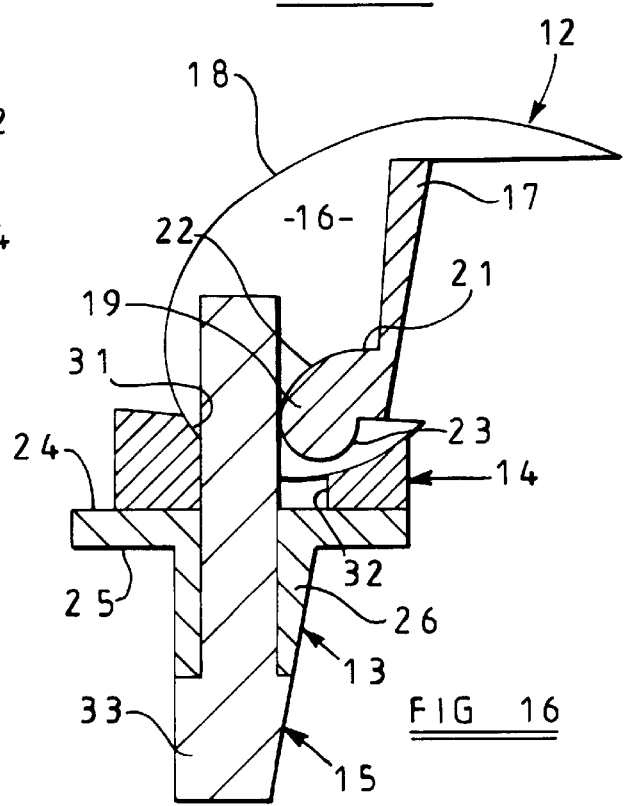

The meniscal component 14 is of a similar shape, in plan view, to the tibial component 13, but would normally be less wide, as shown in FIGS. 14 to 16 so that, as will be explained, even when moved laterally it is still within the width of the tibial component 13 in its two extreme positions shown in FIGS. 14 and 16 respectively. The meniscal component is a bearing body having a planar lower surface 29 which serves, in use, as an articulatory bearing surface engaged with the surface 24 of the tibial component.

An upper surface 30 of the meniscal component is somewhat dished laterally, as schematically shown best in FIGS. 14 to 16, with, as is schematically shown in FIG. 7 also, the surface being higher at its front than at its rear and having a generally smooth curved portion 31 therebetween. As shown best in FIG. 14, the surfaces 18 match the surfaces of part-spherical, preferably hemispherical, indents 30a (FIG. 5) in the surface 30 at respective opposite sides of a slot 32 through component 14, so that the femoral component is congruent with the meniscal component over the normal range of knee joint movement, i.e. that shown through FIGS. 14 to 16, namely from straight to approximately 100° of flexion. These part-spherical portions thus serve as articulatory bearing surfaces. The meniscal component is preferably produced from plastics material, for example Ultra High Molecular Weight Polyethylene (UHMPE). Extending through the meniscal component from its upper to its lower surface, and at approximately the centre of said component is said slot 32, which is in the form of a laterally extending, elongated slot.

Figure 8:
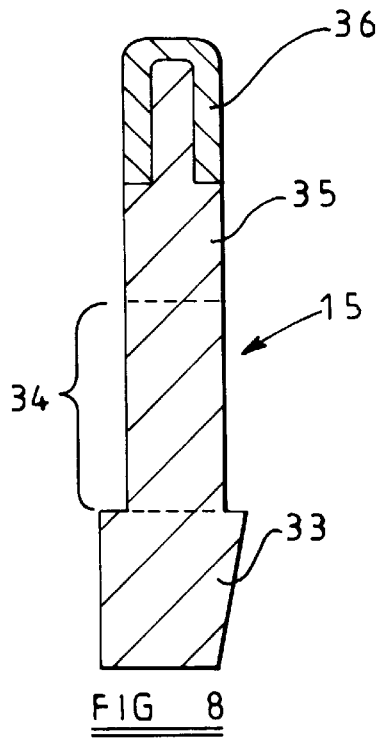
FIG. 8 is a longitudinal centre section of a stabilizing peg forming location means of the knee prosthesis of the invention.
Figure 9:
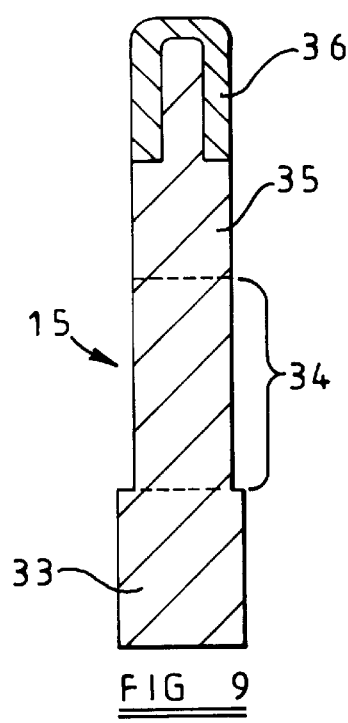
FIG. 9 is a longitudinal centre section of the stabilizing peg at 90° to the section of FIG. 8, FIGS. 10 to 12 are a rear view, a side view and a central vertical sectional view respectively of a femoral component of the knee prosthesis of the invention.

FIGS. 8 and 9 show the stabilizing peg 15 which extends from the tibia 11, through the tibial and meniscal components 13, 14 respectively and into the inter-condylar notch or opening 16 in the femoral component 12. The peg, which is a metallic component, has a distal part in the form of an externally tapered keel 33. A length of the peg immediately above the keel can be in the form of a Morse taper, a typical extent of the taper being indicated by the numeral 34 in FIGS. 8 and 9. Any suitable arrangement for securing the peg to the tibia can be employed. In the embodiment shown in FIGS. 14 to 16, the keel 33 is disposed in engagement with the bottom of the keel 26 of the tibial component, the junction of the keel 33 with the Morse taper defining an annular shoulder against which the annular bottom surface of the keel 26 engages. With this arrangement it can seen that the taper of the exterior surface of the keel 26 matchingly corresponds with the external tapering of the keel 33 so as to form a continuous surface between the keels 26 and 33, the Morse taper being received as a tight interference fit within the bore 27 and aligned hole 28. The lower end of the peg can be of an alternative suitable form from that shown, for securement to the tibia. An example of such an alternative is a distal screw mechanism, with, also for example, a hemispherical free end.

With any of the methods of fixing described, the next, upwards section of the peg is received through the slot 32 in the meniscal component 14. The part of the peg within this slot is a cylindrical portion 35 having a polished metal surface, the height of the surface varying with the thickness of the meniscal component which is used. For example there could be five different thicknesses of meniscal component, with a correspondingly different number of pegs being available, each with a different height of surface portion 35. The diameter of the portion 35 is substantially equivalent to the lateral, i.e. the narrower, width of the slot 32, which is formed with parallel straight sides and opposite rounded ends, the curvature of each end substantially matching the curvature of the portion 35. Accordingly the peg allows the meniscal component unconstrained rotational movement, with limited antero-posterior translation. The peg can be formed with a reduced diameter top portion to receive a cap 36 of UHMWPE material since, as will be described in relation to FIGS. 14 to 16, the top of the peg engages with the projection 19 to provide a cam mechanism which ensures normal posterior translation of the femur upon the tibia during flexion of the knee. For convenience the peg is shown in one section, i.e. without a separate cap 36, in FIGS. 14 to 16 although the cap or an equivalent bearing surface at the end of the peg would normally be present. Although, conveniently, the peg is a component separate from, but securely engaged with the tibial component, it could be integral therewith.

In use, operation of the knee prosthesis is as shown in FIGS. 14 to 16.

FIG. 14 shows the arrangement where the knee is unflexed so that the femur and tibia are generally aligned. With this arrangement it can seen that the surfaces 18 of the femoral component 12 are complimentarily engaged on respective surfaces 31 of the indents in surface 30 of the meniscal component 14. The meniscal component 14 is arranged so that its front surface is at, and generally aligned with, the front surface of the platform of the tibial component 13. As previously described, the peg 15 and the tibial component 13 are securely engaged to the tibia 11, and in the arrangement shown in FIG. 14 the cylindrical portion 35 of the peg is received in the slot 32 towards the far end thereof remote from the front face of the tibial component 13. The upper end of the peg, normally in the form of the cap 36, is adjacent to or in contact with the front surface 21 of the projection 19 of the femoral component 12.

If the knee is then partly flexed, as shown in FIG. 15, there is a camming action, with the engagement between the top of the peg 15 and the projection 19 changing somewhat so that the arcuate surface 22 moves relatively into engagement with the top of the peg 15, with the respective surfaces 18 still maintaining congruence with the surfaces of the indents 30a, as schematically shown in the drawing. Additionally it can seen from FIG. 15 that as a result of the camming action the meniscal component 14 has moved rearwardly on the surface 24 of the tibial component, this being permitted by the peg in the slot 32, as previously described, any sidewards, non-rotational movement, however being prevented by the diameter of the portion 35 matching the lateral width of the slot 32.

As the knee continues to be flexed, the camming action continues, until the position shown in FIG. 16 is reached, where, at approximately 100° of flexion, the engagement at the top of the peg 15 is now with the further arcuate surface 23. The peg is still in the opening, and the respective surfaces 18 are still effectively congruent with the surfaces of the indents 30a. The meniscal component 14 has now moved fully rearwardly to its extreme position, in that further rearwards movement is prevented by the engagement of the peg at the front end of the slot 32, the front face of the meniscal component 14 now being displaced inwardly from the front face of the tibial component 13. Clearly unflexing of the knee would produce relative movements in the reverse order to those shown. As well as allowing backward and forwards movement of the meniscal component, the arrangement also allows said component to rotate relatively about the cylindrical portion 35 of the peg within the slot 32, thereby allowing normal rotational knee movements.

The knee prosthesis thus provides the advantages of a posterior stabilised knee with the 'cam' mechanism, thus ensuring normal posterior translation of the femur upon the tibia during flexure of the knee, whilst at the same time allowing congruence between the femoral component and the meniscal component, thus minimising meniscal wear and minimising rotational and shear stresses on the prosthetic component fixation, in particular tibial stress associated with two-part knees. The particular configurations of the respective surfaces 18 and the 'matching' surfaces of the indents can of course be of any suitable form, and thus different from those illustrated.

I claim:
1. A knee prosthesis comprising a femoral component for securement to the femur, an opening defined by the femoral component, a tibial component for securement to the tibia, an opening through the tibial component, a bearing component between the femoral and tibial components, the femoral component and the bearing component having respective curved articulatory bearing surfaces of congruent form, an elongated slot in the bearing component, a locator separate from the tibial component, a stem part of the locator extending from an enlarged part thereof, the stem part extending through said opening in the tibial component, through said elongated slot in the bearing component, and into said opening defined by the femoral component, the bearing component being capable of rotational movement about the locator, and the elongated slot in the bearing component having a width, such as to prevent relative lateral movement between the locator and the bearing component, and a length to allow linear movement of the bearing component relative to the locator along one path, said linear movement occurring, in use, upon flexion of the knee, and said enlarged part of the locator being disposed at an opposite side of the tibial component to that at which the bearing component engages, and being oversized relative to said opening through the tibial component so as to prevent passage of said enlarged part therethrough.

2. A knee prosthesis as claimed in claim 1, wherein the locator comprises a peg.

3. A knee prosthesis as claimed in claim 2, wherein the part of the peg extending through the bearing component is of circular external cross-section.

4. A knee prosthesis as claimed in claim 3, wherein a portion of said stem part of the peg extending through said elongated slot has an external surface of metal.

5. A knee prosthesis as claimed in claim 4, wherein said external surface is of polished metal.

6. A knee prosthesis as claimed in claim 4, wherein the bearing component is of plastics material.

7. A knee prosthesis as claimed in claim 2, wherein the opening defined by the femoral component is between a pair of condylar members together providing one of said congruent bearing surfaces.

8. A knee prosthesis as claimed in claim 7, wherein the condylar members are connected by a bridge formed with a projection with which said peg engages.

9. A knee prosthesis as claimed in claim 8, wherein said projection is metallic and is engaged by a plastics material tip of said peg.

10. A knee prosthesis as claimed in claim 8, wherein the projection has a flat surface with which the peg engages in an unflexed state of the knee.

11. A knee prosthesis as claimed in claim 10, wherein the projection has first and second arcuate surfaces with which the peg sequentially engages as the knee is moved from an unflexed to a fully flexed state, in use, the first and second arcuate surfaces being of respective different radii of curvature.

12. A knee prosthesis as claimed in claim 10 wherein the engagement of the peg and the bearing component with the femoral component is such that upon the flexion of the knee, in use, the bearing component effects said linear movement over the tibial component.

13. A knee prosthesis as claimed in claim 12, wherein in the unflexed state of the knee the respective congruent bearing surfaces of the femoral component and the bearing component engage at both lateral sides of the peg, whilst in the fully flexed state of the knee such engagement is substantially at one lateral side only, namely that side which moves away from the peg as said linear movement of the bearing component takes place, in use.

14. A knee prosthesis as claimed in claim 1, in which the bearing component has a planar surface at its opposite side to its bearing surface, which flat surface engages a planar surface of the tibial component.

15. A knee prosthesis as claimed in claim 1, wherein said enlarged part of the locator is a keel secured against the tibial component.

16. A knee prosthesis as claimed in claim 1, wherein the femoral component is of tricompartmental form.

17. A kit of parts for a knee prosthesis comprising:
at least one tibial component having an opening and being associable to a tibia in a patient;
at least one bearing component associable with said at least one tibial component;
at least one femoral component associable to a femur of said patient;
at least one locator passable through said opening in said at least one tibial component and at least one bearing component from a surface of said tibial component opposite a surface of said tibial component associable with said bearing component, said locator including an enlarged end adapted to be retained adjacent said surface of said tibial component opposite said surface associable with said bearing component, whereby upon assembly of said components, a knee prosthesis is created.

18. A knee prosthesis kit comprising:
a plurality of tibial components varying in dimension;
a plurality of bearing components varying in dimension, each fitable to at least one of said plurality of tibial components, each bearing component including an elongated slot centrally therethrough;
a plurality of locators of varying dimension securable through at least one of said plurality of tibial components and through said elongated slot of at least one of said plurality of bearing components;
a plurality of femoral components varying in dimension, each combinable with a combination of at least one of said plurality of bearing components and at least one of said plurality of tibial components and at least one of said plurality of locators to assemble a knee prosthesis dimensionally tailored to a particular patient.

* * * * *